United States Patent
Arless et al.

(10) Patent No.: US 6,241,718 B1
(45) Date of Patent: Jun. 5, 2001

(54) METHOD FOR INHIBITING RESTENOSIS

(75) Inventors: Steven G. Arless, Beaconsfield; Daniel Nahon, Ottawa; Jean-Francois Tanguay, Montroyal, all of (CA)

(73) Assignee: CryoCath Technologies, Inc., Kirkland (CA)

(*) Notice: Subject to any disclaimer, the term of this patent is extended or adjusted under 35 U.S.C. 154(b) by 0 days.

(21) Appl. No.: 09/201,068

(22) Filed: Nov. 30, 1998

(51) Int. Cl.[7] .................................................. A61M 31/00
(52) U.S. Cl. ............................................................ 604/509
(58) Field of Search ........................ 606/20–26; 604/509, 604/43

(56) References Cited

U.S. PATENT DOCUMENTS

| | | | |
|---|---|---|---|
| 4,685,458 | 8/1987 | Leckrone | 128/303.1 |
| 4,709,698 | 12/1987 | Johnston et al. | 128/303.12 |
| 4,748,982 | 6/1988 | Horzewski et al. | 128/344 |
| 4,754,752 | 7/1988 | Ginsburg et al. | 128/303.12 |
| 4,771,777 | 9/1988 | Horzewski et al. | 128/344 |
| 4,860,744 | 8/1989 | Johnson et al. | 128/303.1 |
| 4,924,863 | 5/1990 | Sterzer | 606/27 |
| 4,998,933 | 3/1991 | Eggers et al. | 606/41 |
| 5,078,713 | 1/1992 | Varney | 606/23 |
| 5,108,390 | 4/1992 | Potocky et al. | 606/21 |
| 5,114,423 | 5/1992 | Kasprzyk et al. | 606/27 |
| 5,139,496 | 8/1992 | Hed | 606/23 |
| 5,147,355 | 9/1992 | Friedman et al. | 606/23 |
| 5,275,595 | 1/1994 | Dobak, III | 606/23 |
| 5,281,215 | 1/1994 | Milder | 606/20 |
| 5,370,608 | * 12/1994 | Sahota et al. | 604/20 |
| 5,403,309 | 4/1995 | Coleman et al. | 606/20 |
| 5,417,653 | * 5/1995 | Sahota et al. | 604/20 |
| 5,417,689 | 5/1995 | Fine | 606/41 |
| 5,419,760 | * 5/1995 | Narciso, Jr. | 604/8 |
| 5,452,582 | * 9/1995 | Longsworth | 62/51.2 |
| 5,531,742 | 7/1996 | Barken | 606/21 |
| 5,667,505 | 9/1997 | Straus | 606/24 |
| 5,716,353 | 2/1998 | Matsuura et al. | 606/22 |
| 5,775,338 | * 7/1998 | Hastings | 128/898 |
| 5,800,486 | 9/1998 | Thome et al. | 607/105 |
| 5,800,487 | 9/1998 | Mikus et al. | 607/105 |
| 5,800,488 | 9/1998 | Crockett | 607/105 |
| 5,807,391 | 9/1998 | Wijkamp | 606/23 |
| 5,833,685 | 11/1998 | Tortal et al. | 606/23 |
| 5,860,970 | 1/1999 | Goddard et al. | 606/23 |
| 5,868,735 | 2/1999 | Lafontaine | 606/21 |
| 5,971,979 | * 10/1999 | Joye et al. | 606/21 |

\* cited by examiner

*Primary Examiner*—Sharon Kennedy
*Assistant Examiner*—Catherine Serke
(74) *Attorney, Agent, or Firm*—Gunster, Yoakley & Stewart, P.A.

(57) ABSTRACT

A method for inhibiting restenosis includes applying cryogenic energy to a treatment site for a predetermined amount of time. In one embodiment, the treatment site, e.g., a region of an artery dilated by means of a balloon catheter, is cooled to a temperature of about minus fifty degrees Celsius for about two minutes. The application of cryogenic energy inhibits restenosis of the dilated region of the vessel.

9 Claims, 2 Drawing Sheets

METHOD FOR INHIBITING RESTENOSIS

CROSS REFERENCE TO RELATED APPLICATIONS

Not Applicable.

STATEMENT REGARDING FEDERALLY FUNDED RESEARCH

Not Applicable.

FIELD OF THE INVENTION

The present invention relates generally to inhibiting restenosis, and more particularly to treating tissue with cryogenic energy to inhibit restenosis.

BACKGROUND OF THE INVENTION

It is well known to perform an angioplasty procedure to open an arterial vessel that is occluded due to arteriosclerosis, for example. Typically, a balloon catheter is inserted into the patient's arterial network and manipulated to the occluded region of the vessel which is generally proximate the heart. The balloon portion of the catheter is inflated so as to compress the arterial plaque against the vessel walls. The luminal area of the vessel is thereby increased which allows more blood to flow through the vessel.

While the angioplasty procedure may initially be successful, a significant percentage of patients experience restenosis of the treated area. That is, the opened region of the vessel gradually recloses in a relatively short amount of time, such as about six months. Although the exact mechanism is not understood, restenosis is generally believed to involve platelet aggregation, thrombus formation, and smooth cell migration and proliferation, either singly or in combination. However it occurs, restenosis ultimately negates the benefits achieved by the angioplasty procedure.

In order to prevent mechanical recoil of the vessel wall where the balloon is inflated, as well as to mitigate the effects of restenosis, a stent may be implanted in the opened region of the vessel after the angioplasty procedure. As known to one of ordinary skill in the art, a typical stent has a generally cylindrical shape to conform to the vessel and can be formed from a wire mesh. However, stents may irritate the vessel wall. Further, in some patients stents are believed to be the cause of rapid tissue growth, or intimal hyperplasia, through openings in the stent walls.

It would, therefore, be desirable to provide a technique to inhibit restenosis of a vessel region treated with a balloon catheter.

SUMMARY OF THE INVENTION

The present invention provides a technique to minimize restenosis of a dilated region of a blood vessel. In one embodiment, a method of inhibiting restenosis in accordance with the present invention includes applying cryogenic energy to a dilated region of a blood vessel for a predetermined amount of time. A variety of cryogenic systems can be used to cool the target tissue. Exemplary systems include cryogenic catheters having a thermally transmissive distal tip with an elongate and/or rounded geometry. The distal tip can be selectively deformable from a linear shape to an arcuate configuration for achieving contact with the desired tissue.

In an exemplary procedure, the cryogenic catheter is inserted into the patient's arterial network and manipulated to a dilated region of the vessel. Alternatively, the cryogenic catheter forms a portion of a percutaneous transluminal coronary angioplasty (PTCA) assembly which includes the use of a balloon catheter. After the balloon is inflated to open the occluded region of the vessel, the cryogenic catheter is energized to cool the treated site to a selected temperature. If a stent is to be placed in the vessel, it is understood that cryotreatment of the dilated vessel region can be done before, during, and/or after implantation of the stent. An exemplary treatment temperature ranges from about zero degrees Celsius to about one hundred and twenty degrees Celsius for a duration in the range from about ten seconds to about sixty minutes. In one embodiment, the catheter cools the tissue to about minus fifty degrees Celsius for about two minutes.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides a method for treating a dilated vessel region with cryogenic energy for a predetermined amount of time to inhibit restenosis of the treatment site. Typically, an occluded region of the vessel is dilated by means of a percutaneous transluminal coronary angioplasty (PTCA) which includes the use of a balloon catheter. The catheter is inserted into the patient, in the groin area for example, and manipulated to the occluded region of the patient's artery. The balloon is then inflated so as to increase the luminal area of the vessel and thereby increase blood flow through the artery. A stent, which is expandable by the balloon catheter, can be placed within the treated area to prevent mechanical recoil of the vessel wall.

In accordance with the present invention, a cryogenic catheter is utilized to cool the dilated region of the vessel to inhibit restenosis. In general, a cryogenic catheter is inserted into the patient's vascular network and manipulated to a treatment site. The catheter is then energized so as to cool the tissue at the treatment site to a predetermined temperature for a desired amount of time. It is understood that a variety of cryogenic catheter configurations can be used to apply cryogenic energy levels to the treatment site.

Figure 1:
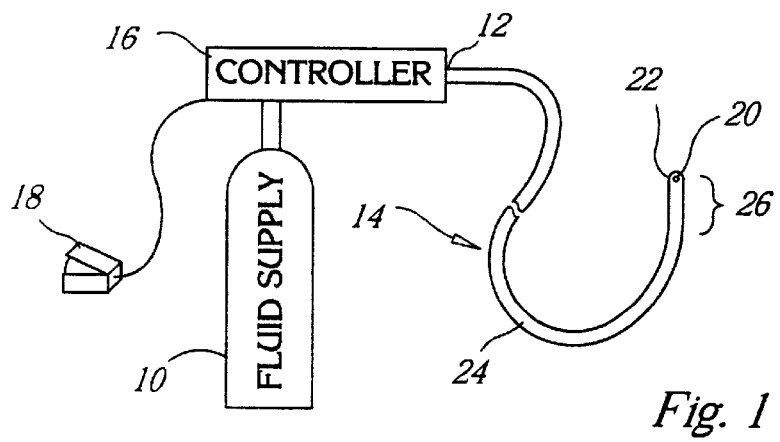
FIG. 1 is a schematic diagram of a cryosurgical system including a catheter for use in conjunction with the present invention.

FIG. 1 is a schematic illustration of an exemplary cryosurgical system for use with the method of the present invention. The system includes a supply of cryogenic or cooling fluid 10 in communication with the proximal end 12 of a flexible catheter 14. A fluid controller 16 is interposed or in-line between the cryogenic fluid supply 10 and the catheter 14 for regulating the flow of cryogenic fluid into the catheter in response to a controller command. Controller commands can include programmed instructions, sensor signals, and manual user input. For example, the fluid controller 16 can be programmed or configured to increase and decrease the pressure of the fluid by predetermined pressure increments over predetermined time intervals. In another exemplary embodiment, the fluid controller 16 can be responsive to input from a foot pedal 18 to permit flow of the cryogenic fluid into the catheter 14. One or more temperature sensors 20 in electrical communication with the controller 16 can be provided to regulate or terminate the flow of cryogenic fluid into the catheter 14 when a predetermined temperature at a selected point or points on or within the catheter is/are obtained. For example, a temperature sensor can be placed at a point proximate the distal end 22 of the catheter and other temperature sensors 20 can be placed at spaced intervals between the distal end of the catheter and another point that is between the distal end and the proximal end.

The catheter 14 includes a flexible member 24 having a thermally-transmissive region 26 and a fluid path through the flexible member to the thermally-transmissive region. A fluid path is also provided from the thermally-transmissive region to a point external to the catheter, such as the proximal end 12. Exemplary fluid paths include one or more channels defined by the flexible member 24, and/or by one or more additional flexible members that are internal to the first flexible member 24. Also, even though many materials and structures can be thermally conductive or thermally transmissive if chilled to a very low temperature and/or cold soaked, as used herein, a "thermally-transmissive region" is intended to broadly encompass any structure or region of the catheter 14 that readily conducts heat.

Furthermore, while the thermally-transmissive region 26 can include a single, continuous, and uninterrupted surface or structure, it can also include multiple, discrete, thermally-transmissive structures that collectively define a thermally-transmissive region that is elongate or linear. Depending on the ability of the cryogenic system, or portions thereof, to handle given thermal loads, the ablation of an elongate tissue path can be performed in a single or multiple cycle process without having to relocate the catheter one or more times or drag it across tissue.

In some embodiments, the thermally-transmissive region 26 of the catheter 14 is deformable. An exemplary deformation is from a linear configuration to an arcuate configuration and is accomplished using mechanical and/or electrical devices known to those skilled in the art. For example, a wall portion of the flexible member 24 can include a metal braid to make the catheter torqueable for overall catheter steering and placement. Additionally, a cord, wire or cable can be incorporated with, or inserted into, the catheter for deformation of the thermally transmissive region 26. Further, a balloon can be incorporated into the thermally transmissive region 26 such that the catheter can dilate the occluded region of the vessel as well as treat the dilated region with cryogenic energy.

Figure 2:
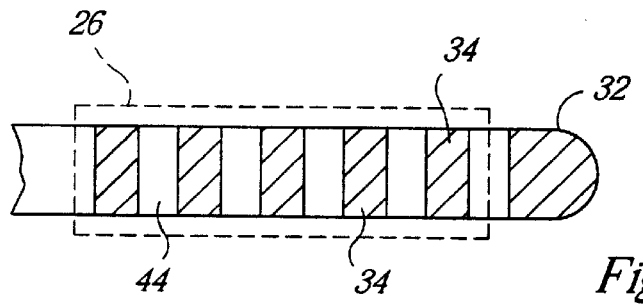
FIG. 2 is a side view of a tip region of the catheter of FIG. 1.
Figure 3:
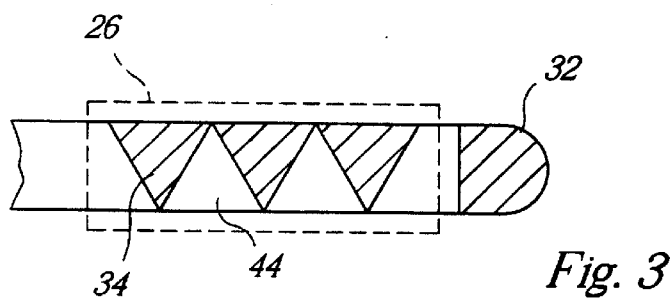
FIG. 3 is a side view of an alternative embodiment of the catheter tip region of the FIG. 2.
Figure 4:
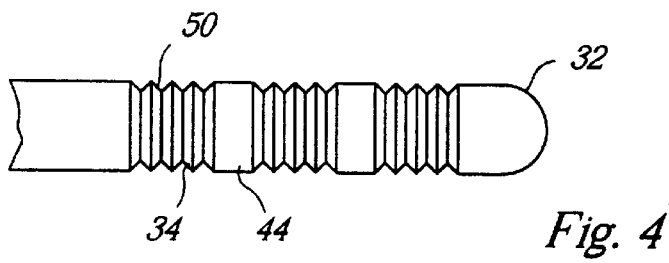
FIG. 4 is a side view of another embodiment of the catheter tip region of FIG. 1.

In other embodiments, such as those shown in FIGS. 2, 3 and 4 for example, the catheter, or portions thereof, have two or more thermally-transmissive segments in a spaced-apart relationship. Each of the illustrated catheters includes a closed tip 32 that can include a thermally-transmissive material.

With respect to the embodiments shown in both FIGS. 2 and 3, the thermally-transmissive elements 34 are substantially rigid and are separated and/or joined by a flexible material 44. However, in other embodiments the thermally-transmissive elements 34 are flexible and are interdigitated with either rigid or flexible segments. FIG. 4, for example, illustrates an embodiment of the cryogenic catheter having three thermally-transmissive elements 34 that are flexible. The flexibility is provided by a folded or bellows-like structure 50. In addition to being shapable, a metal bellows can have enough stiffness to retain a selected shape after a deforming or bending step.

Figure 5:
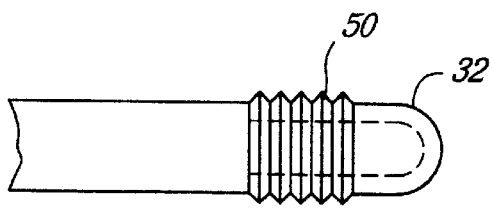
FIG. 5 is a side view of a further embodiment of the catheter tip region of FIG. 1.

Instead of, or in addition to, flexible, thermally-transmissive elements 34 and/or flexible material 44 between elements, the distal tip 32 (or a portion thereof) can be deformable. For example, FIG. 5 illustrates a tip 32 having thermally-transmissive, flexible, bellows 50.

Figure 6:
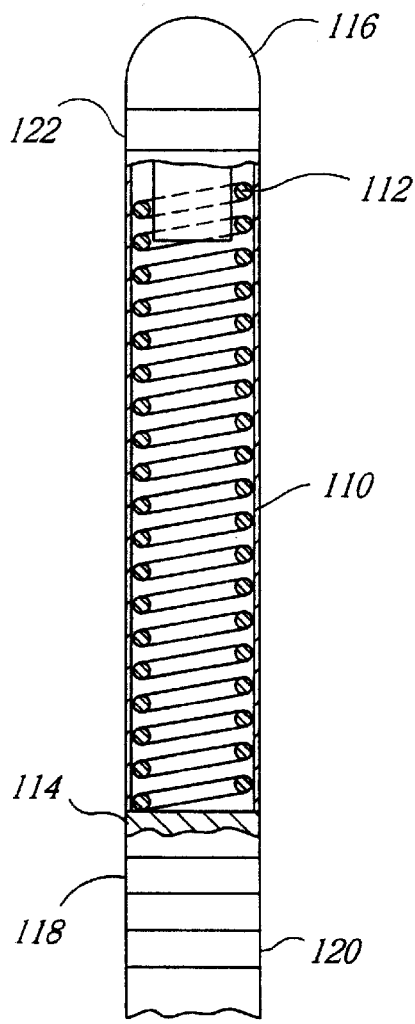
FIG. 6 is a partial cutaway of a side view of yet another embodiment of the catheter of FIG. 1.

FIG. 6 illustrates another embodiment of a cryogenic cooling structure that includes a surface or wall 110 including a polymer or elastomer that is thin enough to permit thermal transfer. For example, polyamide, PET, or PTFE having a thickness of a typical angioplasty balloon or less (below 0.006 inches) provides acceptable thermal transfer. However, the thinness of the wall 110 allows it to readily collapse or otherwise deform under vacuum or near vacuum conditions applied to evacuate fluid/gas from the structure. Accordingly, the structure is provided with one or more supporting elements 112 such as a spring. The cooling structure is illustrated in association with a catheter 114 having a closed distal tip 116 and mono or bipolar ECG rings 118, 120, 122. The thermally-transmissive region is approximately 30 mm in length and is effective for thermal transfer over its entire circumference. However, the thermally-transmissive region can be confined to specific region(s) of the device's circumference.

It is understood that other types of cryogenic catheters having differing types of distal tips can be used. Further exemplary catheters that can be used in conjunction with the method of the present invention are shown and described in co-pending and commonly assigned U.S. patent application Ser. No. 08/893,825, filed on Jul. 11, 1997, incorporated herein by reference.

In an exemplary procedure, a cryogenic catheter having a ten millimeter cooling segment with a five French diameter, which can be obtained from CryoCath Technologies Inc. of St. Laurent, Quebec, Canada, is inserted into the patient's arterial network. The catheter is then manipulated to a region of the vessel that is dilated using a conventional PTCA, for example. A distal tip of the catheter is positioned so as to contact the dilated region of the vessel. The catheter is then energized so as to cool the tissue in contact with the distal tip of the catheter.

Cryogenic energy can be applied to the treatment site in a wide range of temperatures and for various time intervals depending on the desired effect. For example, energy can be applied such that the tissue temperature is constant or it can vary. Further, energy can be applied for one or more predetermined time intervals at the same or different temperatures. The time intervals can vary as well, so as to achieve a desired level of cryogenic treatment for the target tissue. Also, certain areas of the treatment site may be cooled to a greater or lesser extent than surrounding target tissue.

In general, the tissue at the treatment site, e.g., the dilated region of the vessel, is cooled to a temperature in the range from about zero degrees Celsius to about minus one hundred and twenty degrees Celsius for a period of time ranging from about ten seconds to about sixty minutes. It is understood that as tissue is cooled to more extreme temperatures the duration of the treatment can be decreased. In one embodiment, the treatment site is cooled to a temperature of about minus fifty degrees Celsius for about two minutes.

In contrast with heat and radiation tissue treatments, the application of cryogenic energy produces less damage to the arterial wall structure. The damage reduction occurs because a freeze injury does not significantly alter the collagen structure as compared with the application of heat. Further, a freeze injury does not significantly reduce the reproductive/repair capability of the living tissue as compared with radiation treatments.

Figure 7:
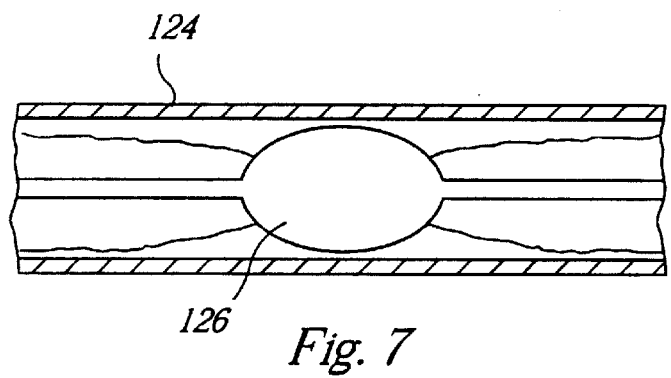
FIG. 7 is a pictorial diagram of a balloon catheter inflated within an artery.

As shown in FIG. 7, cryogenic energy can be applied to a vessel region 124 dilated with a balloon catheter 126, wherein the balloon catheter is infused with a cryogenic fluid and maintained in contact with tissue for a period of time as described above. Although this procedure can have a restenosis effect, a surgeon may also wish to implant a stent. Thus, in another exemplary procedure, a balloon dilated region of a vessel is treated with cryogenic energy prior to implantation of a vascular stent. By treating the tissue with cryogenic energy, rapid tissue growth or so-called remodeling commonly associated with implanted stents is believed to be reduced or substantially prevented.

Figure 8:
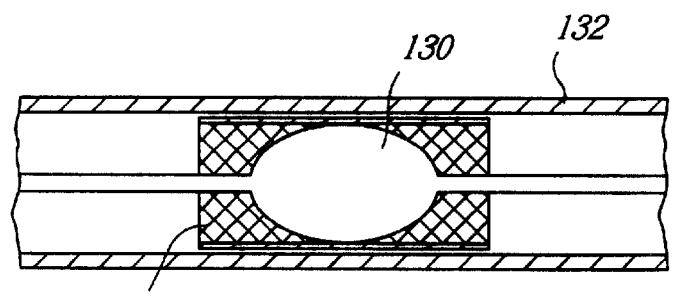
FIG. 8 is a pictorial diagram of a stent being expanded by a balloon catheter.

As shown in FIG. 8, a stent 128 can be expanded by a cryoballoon catheter following the cryo-treatment of a vessel 132 or simultaneous with the cryo-treatment. Also, the stent can be expanded and then cryo-treatment can begin.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for inhibiting restenosis, comprising:

cooling a blood vessel and surrounding tissue at a treatment site to a temperature in the range from less than about zero degrees Celsius to about minus one hundred and twenty degrees Celsius for a period of time in the range from about ten seconds to about sixty minutes such that the blood vessel and surrounding tissue retain the ability to reproduce and repair themselves after treatment thereby inhibiting resteirosis.

2. The method according to claim 1, wherein the temperature of the treatment site is between about minus forty and minus sixty degrees Celsius.

3. The method according to claim 1, wherein the temperature of the treatment site is about minus fifty degrees Celsius.

4. The method according to claim 1, wherein the period of time is between about one hundred seconds and about one hundred and forty seconds.

5. The method according to claim 4, wherein the period of time is about one hundred and twenty seconds.

6. A method for inhibiting restenosis, comprising:

inserting a catheter into a patient's arterial network;

manipulating the catheter to a dilated region of an artery such that an outer surface of the catheter contacts tissue within a region of the artery which was dilated with a balloon catheter;

energizing the catheter such that the outer surface of the catheter cools the contacting tissue to a temperature of less than about zero degrees Celsius;

cooling the contacting tissue for a period of time that is greater than about ten seconds such that the tissue retains the ability to reproduce and repair itself after treatment; and removing the catheter from the patient's arterial network.

7. The method according to claim 6, wherein the temperature is greater than about minus one hundred and twenty degrees Celsius.

8. The method according to claim 6, wherein the temperature is between about minus forty degrees Celsius and about minus sixty degrees Celsius.

9. The method according to claim 6, wherein the temperature is about minus fifty degrees Celsius.

* * * * *

UNITED STATES PATENT AND TRADEMARK OFFICE
CERTIFICATE OF CORRECTION

PATENT NO. : 6,241,718 B1
DATED : June 5, 2001
INVENTOR(S) : Steven G. Arless et al.

It is certified that error appears in the above-identified patent and that said Letters Patent is hereby corrected as shown below:

Column 6,
Line 5, "resteirosis" should read -- restenosis --.

Signed and Sealed this

Twenty-first Day of June, 2005

JON W. DUDAS
*Director of the United States Patent and Trademark Office*